US006677602B1

(12) United States Patent
Norton

(10) Patent No.: US 6,677,602 B1
(45) Date of Patent: Jan. 13, 2004

(54) NOTCH AND FLAT SENSOR FOR WAFER ALIGNMENT

(75) Inventor: Adam E. Norton, Palo Alto, CA (US)

(73) Assignee: Sensys Instruments Corporation, Santa Clara, CA (US)

( * ) Notice: Subject to any disclaimer, the term of this patent is extended or adjusted under 35 U.S.C. 154(b) by 67 days.

(21) Appl. No.: 09/932,786

(22) Filed: Aug. 17, 2001

Related U.S. Application Data

(60) Provisional application No. 60/226,418, filed on Aug. 18, 2000.

(51) Int. Cl.[7] .................................................. G01N 21/86

(52) U.S. Cl. ................................. 250/559.3; 250/559.4; 250/559.36; 250/559.29

(58) Field of Search ........................... 250/203.3, 203.2, 250/548, 559.3, 400, 559.29, 559.36, 559.4; 356/3.08, 4.06, 435, 434

(56) References Cited

U.S. PATENT DOCUMENTS 3,671,748 A * 6/1972 Friedman .................... 250/201
5,684,599 A * 11/1997 Shimoyama et al. ....... 356/400

FOREIGN PATENT DOCUMENTS

JP 62-076643 * 4/1987

* cited by examiner

*Primary Examiner*—Stephen D. Meier
*Assistant Examiner*—Lam Nguyen
(74) *Attorney, Agent, or Firm*—Stallman & Pollock LLP

(57) ABSTRACT

A notch or flat sensor for a semiconductor wafer on a wafer stage or support includes a dual photodiode detector arrangement located at the edge position of the wafer. Each photodiode element has substantially equal coverage of the wafer edge when the wafer's notch or flat is not proximate to the detector, but has different coverage from the other photodiode when the notch or flat is proximate to the detector. A light source illuminates the edge of the wafer opposite the detector arrangement. Comparison of the light intensity sensed by each photodiode, e.g. by means of a differential amplifier circuit and threshold sensor, reveals the position of the notch or flat.

15 Claims, 2 Drawing Sheets

17 11 13 19 21 15a 15b 29 27 17 25 23

NOTCH AND FLAT SENSOR FOR WAFER ALIGNMENT

CROSS-REFERENCE TO RELATED APPLICATION

The present application claims priority under 35 U.S.C. §119(e) from prior U.S. provisional application No. 60/226,418, filed Aug. 18, 2000.

TECHNICAL FIELD

The invention relates to wafer stages for supporting, rotating and aligning semiconductor wafers, especially for use in wafer process stations and inspection stations. The invention relates in particular to methods and apparatus for detecting notches and flat edges that are provided on wafer edges for establishing a reference position of such wafers.

BACKGROUND ART

Semiconductor wafer processing or metrology equipment frequently needs a device to orient the wafer before the processing or measurement begins. This type of equipment is almost always controlled by one or more processors. Frequently, such equipment has a video viewing subsystem capable of seeing a magnified view at any point on the wafer's surface. This equipment might also have a pattern recognition subsystem to orient the wafer. However, if there is no pattern recognition, or if the viewing subsystem has a small capture range, or if the wafer is unpatterned, then the wafers must be oriented by detecting notches or flats cut into the edge of the wafer.

There are many existing designs for wafer aligners. One general class of designs use three emitter/detector pairs; two located near where the notch or flat should be and the third where another portion of the edge of the wafer should be. The wafer is then moved in X,Y and theta until the edges partially blocks all three detectors.

Another design spins the edge of the wafer between a light source and a long photodiode. The signal from the photodiode is digitized and analyzed by algorithms to determine the position of the wafer in X, Y and theta. A variation of this technique uses a photodiode array in place of the long photodiode. A problem with most of these techniques is that they require dedicated processors or other complicated electronics that, among other problems, would be difficult to retrofit into equipment not initially designed to have notch or flat aligner.

An object of the present invention is provide a simple wafer aligner that is easily designed into wafer processing or metrology equipment with minimal changes to the electronics and hardware.

DISCLOSURE OF THE INVENTION

The present invention is a wafer alignment sensing system that can be easily incorporating into wafer processing equipment as described above.

The present invention uses a dual photodiode above the wafer. This is mechanically similar to the single long photodiode embodiment described above, except that the detector is a split diode with the gap oriented perpendicular to the edge of the wafer. The outputs of these two diodes are fed into a differential amplifier. As long as the two diodes are covered equally, the output is close to zero. When the notch starts to uncover one diode, the output increases. In effect the detector is sensitive only to the local angle at the edge of the wafer. The main advantage is that now the motor can be rotated until a certain analog threshold is reached at the output without having to digitize the signal. The threshold will not depend on the amount of wafer decenter. This detector is also sensitive to the areas near the corners of flats, and it would find the flat by looking for the thresholds at both corners. The accuracy would depend on the rotation speed and the time required for the electronics and software to respond. If necessary, after the notch is detected, the motor could back up and scan more slowly to find a more accurate position. The center X,Y position could also be found if needed by digitizing the output from only one of the two diodes. To minimize interference from room light we could use a near infrared LED and an IR filter in front of the diode, as is done in television remotes.

An alternative embodiment combines the dual photodiode scheme with large field pattern recognition for edge sensing. The idea here is to use the dual photodiode arrangement only for quickly detecting the rough position of the notch or flat. After that, a pattern recognition implementation like that described above could measure the wafer at the notch or flat and at two other sites on the wafer edge to determine the wafer center X,Y position and theta orientation more accurately. The three pattern recognition measurements would add a couple of seconds, and could be optional if high accuracy is not required. This technique for edge sensing avoids having to digitize or calibrate the diode output. The pattern recognition measurements could be taken either by moving the viewing system to the three points, or by keeping the viewing system fixed near the wafer edge and rotating the wafer to 3 positions.

BEST MODE OF CARRYING OUT THE INVENTION

Notch/flat Finder Details

One goal of this invention is to be able to quickly find the angular orientation of the notch or flat on unpatterned wafers. Once found, the notch can be rotated to a predetermined position by the theta motor. The repeatability should be at least within 200 μm at the edge of the wafer, with a goal of 100 μm. The user should also be able to select the orientation of the notch as part of the software recipe (specified as an integer number of degrees). To aid in system-to-system matching, the position of the notch that triggers the detector must be calibrated relative to the stage axes with 200 μm at the edge of a 200 mm wafer (0.1 deg).

Figure 1:
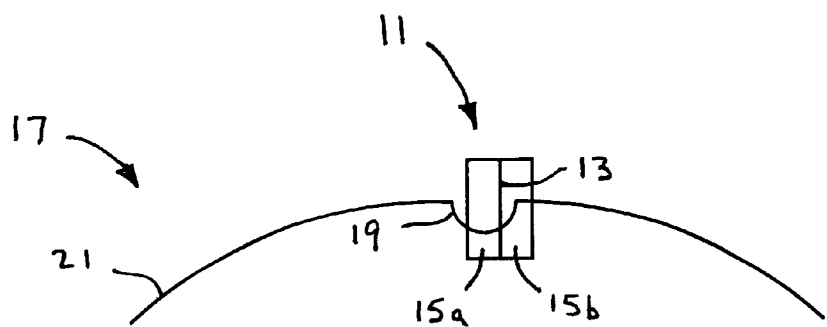
FIG. 1 is a top plan view of a portion of a wafer having a reference position indicator in the form of a notch, showing the orientation of a split photodiode at the edge of the wafer in accord with the present invention.

With reference to FIG. 1, the invention calls for a split photodiode arrangement 11 oriented such that the gap 13 between its two photodiode sensing elements 15*a* and 15*b* is perpendicular to the edge 21 of the wafer 17, as shown. A notch 19 is located in the wafer edge 21 to serve as a reference position indicator for the wafer 17. An LED light source, not seen in this view, illuminates the wafer 17 at its edge 21. To minimize interference from room lights, the source should be an IR LED and the detector should have an IR filter in front. Other photodetectors such as photomultipliers or photocells could be used in place of photodiodes.

Figure 2:
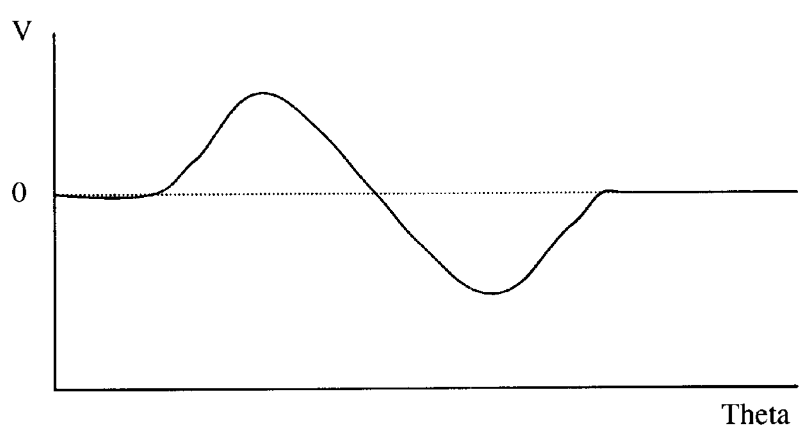
FIG. 2 is a graph of voltage output by a differential amplifier versus wafer rotation angle (theta), detecting a notch according to the present invention.

When the dual photodiode arrangement 11 is proximate to those portions of the wafer edge 21 where the notch is not, the two diodes 15*a* and 15*b* will sense a constant and substantially equal amount of light. When the photodiode arrangement 11 encounters the notch, first one then the other diode 15*a* and 15*b* will sense an increase of received light as the notch passes by the diodes. The output signal from each of the two diodes 15*a* and 15*b* represents the light intensity sensed by that diode. These electrical output signals may be fed into a differential amplifier for comparison. As the wafer 17 rotates on a movable stage, the differential signal versus angular position of the wafer looks like that shown in FIG. 2. The position of each edge of the notch can be found when the magnitude of the differential signal reaches a certain threshold value.

Optical Components

Figure 3:
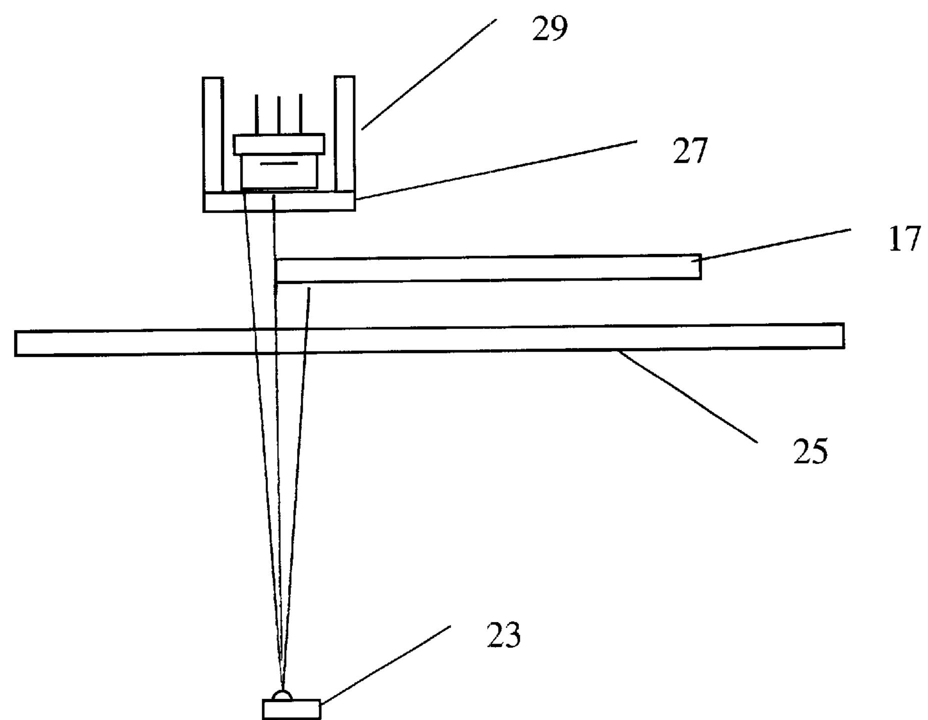
FIG. 3 is a side plan view of a preferred implementation of the notch/edge finder of the present invention.

As seen in FIG. 3, the detector 11 is housed in a small box 29 just above the wafer's edge. The bottom window of this box is an IR transmitting filter 27 that minimizes stray room light and also serves to keep out water when operating in a wet environment such as a chemical mechanical polishing (CMP) system.

The detector 11 itself is a split photodiode with its joint oriented perpendicularly to the edge of the wafer 17, as already seen in FIG. 1. The outputs of the two detectors are fed into a differential amplifier so that the signal changes only when there is a difference in the light falling on the two halves of the diode. For this purpose, the photodiode can be mounted on a small board inside the housing that preferably includes the amplifier.

The length (perpendicular to the wafer edge) of the split diode should be at least 3 mm to accommodate the ±1 mm wafer centering error and the 1 mm notch depth. In addition, the maximum modulation of the signal is achieved when each element is roughly as wide as the 3mm wide notch.

A split diode that meets these requirements is Centrovision P/N CD33H-2D. This dual element photodiode has 3 mm square element dimensions and an 0.3 mm element separation centered within a package or case having a 5.9 mm window diameter. The peak spectral response is at 950 nm, with response times of 0.2 $\mu$s (min.), 200 $\mu$s (typ.), and 15 $\mu$s (at Vr=10V). The dark current for this photodiode is 10 nA (typ.) or 1 nA (at Vr).

A bright IR LED 23 is located roughly 22 mm below the wafer to act as the light source. The LED can be turned on and off by software.

The IR LED 23 must meet the requirements that it have a small effective source size so that it can be placed close to the wafer and detector for maximum intensity without an overly large penumbra. The angular intensity distribution must be also adequate to cover the detector with uniform illumination, but not too large that light is wasted. It must also be as bright as is available for the small source size.

The LED manufacturers do not give enough information to determine the effective source size, using LEDs that have very small lenses puts an upper limit on the source size. One LED that fits is Lumex P/N OED-CL1556SN. This LED is an IR emitting ($\lambda_p$=880 nm) device with an output power P=880 mW and a divergence $\Delta\theta$=±15° in a package with a 1. 5 mm diameter, yellow transparent, hemispheric lens. Brightness is 6.5 mW/sr (typ.) and 50 mW/sr (at $I_f$=60 mA).

The last optical component is the IR filter 27. This also serves as the water-tight window in front of the detector 11. It must survive water immersion, and the best type for that is a colored plastic filter (Edmund Industrial Optics P/N H43954).

The rough layout of all these components is shown in FIG. 3. In this layout, the LED 23 is seen to direct light through an IR transparent window 25 to the wafer 17. The LED is placed on the X-stage close to the wafer plane but with a comfortable gap. A typical distance from LED 23 to wafer 17 is about 22 mm. The IR filter 27 is positioned in front of the two-element photodiode 11, typically about 5.5 mm from the wafer and 3.65 mm from the diode elements. The photodiodes 11 are contained within a diode package or case that is about 9.25 mm wide, which in turn is enclosed around its sides by a 12 mm wide opaque housing. The positions of the filter 27 and detector housing 29 are constrained by the wafer handler design. The maximum penumbra at the detector is less than ±0.3 mm.

While the light from the LED must pass across the wafer edge to the dual photodiode detector, the LED itself need not be physically located opposite detector provided suitable optics (mirrors, etc) are provided to direct the light onto the wafer edge.

Sensitivity

With the geometry shown above, we have 6.5 $\mu$W/mm$^2$ of irradiance falling on the detector. The maximum difference between the two elements of the photodiode occurs when the notch is centered on one element. In this case, the difference in radiant power on the two halves is about 13 $\mu$W. Since the responsivity of the diode is 0.5 A/W, this corresponds to a difference in the current from the two elements of 6.5 $\mu$A.

Where the signal has its maximum slope at the left and right sides of the curve, a 50 $\mu$m translation of the notch causes the difference in the output current to change by 162 nA. Since the dark noise on each detector element is less than 10 nA, it is quite feasible to find the center of the notch to this precision.

For an 8" wafer with a flat, the maximum current difference will be just about half that for a notch, or 3.25 $\mu$A. The left and right slopes are such that a 50 $\mu$m rotation of the wafer edge causes a change in the current difference of 106 nA.

Figure 4:
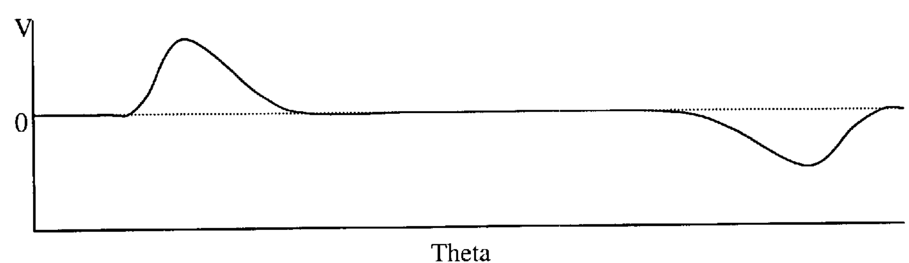
FIG. 4 is a graph of voltage output versus wafer rotation angle (theta), like FIG. 2, except detecting a wafer flat edge according to the present invention.

One difference between flat and notch signals is that the flat is 4.5 mm deep so that it completely uncovers both halves of the detector as it scans across. The signal for a flatted wafer thus looks like that shown in FIG. 4.

Electronics

The analog difference signal from the photodiode board goes to another board that performs the thresholding function (assuming there is not space for this function on the small photodiode board). This board preferably lies outside the wafer process or inspection station with the other electronics. Its job is to detect when the analog difference signal exceeds a predetermined threshold. When the threshold is triggered, it sends a signal to a Motion Engineering Inc. (MEI) motion control board model 104/DSP, which will then save the position of the theta motor at that instant. The MEI board is also used to control the stage motion.

The thresholding board also needs to recognize negative thresholds to detect the other edge of the notch or flat. This can be accomplished simply by having the board trigger when either the signal goes below the negative threshold or above the positive threshold. (The software algorithm I propose below does not need to know which it is.)

The threshold level, however, will likely need to be selectable for each unit and wafer type. This is to accommodate variations in LED brightness and flats versus notches. It would be preferable, but not necessary, if the level could be calibrated and set by the software.

A differential amplifier generates an analog comparison value between the detection signals from the two photodiode elements which is a difference between the magnitudes of those two signals. The differential signal should be substantially zero except when the notch or flat is in proximity to the dual photodiode arrangement. Other comparison values which could be used are a ratio between the magnitudes of the two detection signals, for example, by means of a voltage divider circuit. In that case the ratio would be substantially equal to one except when the notch or flat is in proximity to the detector. Instead of using analog signal comparison, either type comparison value (difference or ratio) could be calculated arithmetically using digital values obtained by using analog-to-digital circuits (ADCs) to convert the analog detection signals from the photodiode elements into corresponding digital values.

Software

There are three major components to the software: graphical user interface (GUI), a low level routine to control notch alignment, and calibration software.

The GUI needs entries in the recipe for selecting notch/flat alignment and for selecting the angle, in integer degrees, for the final position of the notch. It will also have to read from a calibration file values for the threshold level, and the calibrated position of the notch sensor. If both notch/flat finding and pattern recognition are to be done on a wafer, the notch/flat finding is done first.

When the lower level routine is told to find the notch it should do the following (the order of some of these steps may be changed):

1. Move the LED to the correct position with its X-Y stage (if so equipped).
2. Turn on the LED and turn off any other light sources in the system controlled by the software.
3. Set up the MEI board to save the theta position when it receives the trigger signal.
4. Set the threshold level on the threshold board.
5. Rotate the theta motor 360 deg. counter-clockwise at a predetermined constant velocity (the velocity will depend on the noise on the signal and the accuracy required. It will be in the neighborhood of 2 sec. per turn.)
6. Read the triggered theta position from the MEI board.
7. If the position found in step 6 is too close the starting position (i.e. within the width of the flat or notch) back up the starting position and go back to step 5.
8. The position in step 6 is the left side of the notch or flat. From this position, move the stage counter clockwise to a new starting position just beyond where the right edge of a flat would be.
9. Rotate the theta motor clockwise at a constant velocity back to the position found in step 6.
10. Read the theta position stored on the MEI, this is the right side of the notch or flat.
11. If the difference between the left and right edges are too large to be a notch and too small to be the major flat, assume it is a minor flat, advance the starting point beyond the minor flat, and go back to step 5.
12. Otherwise, calculate the midpoint between the left and right sides, this is the center of the notch of flat.
13. Rotate the notch or flat to the position specified in the recipe, use the calibrated offset of the notch detector.
14. Turn off the LED.

The above algorithm should work for flats or notches without the software having to worry which it is searching for.

The calibration software uses a patterned wafer. The notch is found and oriented without any calibrated offset applied. The angle of the wafer is then measured using the pattern recognition at opposite edges of the wafer. The angle is then saved in the calibration file as the offset for the notch finder.

The calibration software will also likely need to find the appropriate threshold value. One technique would be to use a notched or flatted wafer (which ever is appropriate), and increment the threshold until the notch or flat cannot be found. The threshold is then decremented by 50% so that it intersects the signal where the slope is steepest. The threshold value is saved in a calibration file.

What is claimed is:

1. A wafer alignment sensing system, comprising:

a stage capable of supporting and rotating a wafer, said wafer having an edge with a reference position indicator therein;

at least one source providing light that is directed at the wafer edge;

a pair of photodetectors oriented adjacent to each other and separated by a narrow gap, each photodetector extending across the edge of the wafer and positioned such that both photodetectors have substantially equal coverage of the wafer edge except when the reference position indicator is proximate to the photodetectors, each photodetector producing an electrical signal that is a measure of light intensity sensed by that photodetector; and a circuit in electronic signal communication with the dual photodiode arrangement and with an encoder associated with the stage, said circuit storing the position of the stage given by the encoder when the signals from each photodetector in the arrangement are not substantially equal.

2. The system of claim 1 wherein the reference position indicator is a notch formed in the wafer edge.

3. The system of claim 1 wherein the reference position indicator is a flat portion of the generally circular wafer edge.

4. The system of claim 1 further comprising a viewing system disposed to image a portion of the wafer edge, and pattern recognition viewing system coupled to said viewing system for finding a precise position of said reference position indicator and for finding the position of the wafer center.

5. The system of claim 1 wherein the comparing means comprises a differential amplifier coupled to receive the electrical signals from both photodetectors, whereby a differential signal is generated that crosses a threshold when the reference position indicator comes into proximity with the photodetectors.

6. The system of claim 1 wherein the comparing means comprises a digital circuit including analog-to-digital circuits (ADCs) for said electrical signals from the photodetector and an arithmetic processor for calculating the comparison value from the digital values output by the ADCs.

7. The system of claim 1 wherein the comparison value is a difference in the magnitudes between the electrical signals from both photodetectors.

8. The system of claim 1 wherein the comparison value is a ratio between the magnitudes of the electrical signals from both photodetectors.

9. The system of claim 1 further comprising a memory circuit in electronic signal communication with the threshold sensor and with an encoder associated with the stage, the memory circuit storing the stage orientation indicated by the encoder when triggered by the threshold sensor.

10. A wafer alignment sensing system, comprising:

a stage capable of supporting and rotating a wafer, said wafer having an edge with a reference position indicator therein;

at least one source providing light that is directed at the location of the wafer edge;

a dual photodetector arrangement oriented such that both photodetectors of the arrangement have substantially equal coverage of the wafer edge except when the reference position indicator is proximate to the dual photodetector arrangement, each photodetector of the arrangement producing an electrical signal that is a measure of light intensity sensed by that photodetector; and a circuit in electronic signal communication with the dual photodiode arrangement and with an encoder associated with the stage, said circuit storing the position of the stage given by the encoder when the signals from each photodetector in the arrangement are not substantially equal.

11. A wafer alignment sensing system, comprising:

a stage capable of supporting and rotating a wafer, said wafer having an edge with a reference position indicator therein;

at least one source providing light that is directed at the location of the wafer edge;

a dual photodetector arrangement oriented such that both photodetectors of the arrangement have substantially equal coverage of the wafer edge except when the reference position indicator is proximate to the dual photodetector arrangement, each photodetector of the arrangement producing an electrical signal that is a measure of light intensity sensed by that photodetector;

means for comparing the electrical signals from both photodetectors of the arrangement and producing a comparison value that exceeds a threshold whenever the reference position indicator comes into proximity with the dual photodetector arrangement; and a threshold sensor determining when said comparison value exceeds said threshold wherein the comparison value is a ratio between the magnitudes of the electrical signals from both photodetectors.

12. A wafer alignment sensing system, comprising:

a stage capable of supporting and rotating a wafer, said wafer having an edge with a reference position indicator therein;

at least one source providing light that is directed at the location of the wafer edge;

a dual photodetector arrangement oriented such that both photodetectors of the arrangement have substantially equal coverage of the wafer edge except when the reference position indicator is proximate to the dual photodetector arrangement, each photodetector of the arrangement producing an electrical signal that is a measure of light intensity sensed by that photodetector;

means for comparing the electrical signals from both photodetectors of the arrangement and producing a comparison value that exceeds a threshold whenever the reference position indicator comes into proximity with the dual photodetector arrangement;

a threshold sensor determining when said comparison value exceeds said threshold; and a memory circuit in electronic signal communication with the threshold sensor and with an encoder associated with the stage, the memory circuit storing the stage orientation indicated by the encoder when triggered by the threshold sensor.

13. A method of aligning a semiconductor wafer supported on a stage with respect to a reference position indicator provided on an edge of the wafer, comprising:

driving the stage so as to rotate the wafer; illuminating an edge of the wafer with light directed thereat from at least one source;

sensing light intensity received by a dual photodetector arrangement positioned proximate to the wafer edge and oriented such that both photodetectors of the arrangement have substantially equal coverage of the wafer edge except when the reference position indicator passes by the dual photodetector arrangement, each photodetector of the arrangement producing an electrical signal that is a measure of the sensed light intensity by that photodetector; and comparing the electrical signals from both photodetectors and producing a comparison value that exceeds a threshold value whenever the reference position indicator comes into proximity with the dual photodetector arrangement wherein the comparison value is a ratio of the magnitudes between the electrical signals from both photodetectors.

14. A method of aligning a semiconductor wafer supported on a stage with respect to a reference position indicator provided on an edge of the wafer, comprising:

driving the stage so as to rotate the wafer;

illuminating an edge of the wafer with light directed thereat from at least one source;

sensing light intensity received by a dual photodetector arrangement positioned proximate to the wafer edge and oriented such that both photodetectors of the arrangement have substantially equal coverage of the wafer edge except when the reference position indicator passes by the dual photodetector arrangement, each photodetector of the arrangement producing an electrical signal that is a measure of the sensed light intensity by that photodetector wherein the driving of the stage is accomplished successively in opposite rotational directions to record the stage position for the reference position indicator passing by the dual photodetector arrangement in each direction; and comparing the electrical signals from both photodetectors and producing a comparison value that exceeds a threshold value whenever the reference position indicator comes into proximity with the dual photodetector arrangement.

15. A method of aligning a semiconductor wafer supported on a stage with respect to a reference position indicator provided on an edge of the wafer, comprising:

driving the stage so as to rotate the wafer;

illuminating an edge of the wafer with light directed thereat from at least one source;

sensing light intensity received by a dual photodetector arrangement positioned proximate to the wafer edge and oriented such that both photodetectors of the arrangement have substantially equal coverage of the wafer edge except when the reference position indicator passes by the dual photodetector arrangement, each photodetector of the arrangement producing an electrical signal that is a measure of the sensed light intensity by that photodetector; and comparing the electrical signals from both photodetectors and producing a comparison value that exceeds a threshold value whenever the reference position indicator comes into proximity with the dual photodetector arrangement; and recording a position of the stage whenever the threshold sensor indicates the exceeding of the threshold value by the comparison value.

* * * * *